US011426538B2

(12) United States Patent
Copelli et al.

(10) Patent No.: US 11,426,538 B2
(45) Date of Patent: Aug. 30, 2022

(54) AEROSOL INHALATION DEVICE

(71) Applicant: CHIESI FARMACEUTICI S.p.A., Parma (IT)

(72) Inventors: Diego Copelli, Parma (IT); Andrea Casazza, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 169 days.

(21) Appl. No.: 15/475,649

(22) Filed: Mar. 31, 2017

(65) Prior Publication Data

US 2017/0281885 A1 Oct. 5, 2017

(30) Foreign Application Priority Data

Mar. 31, 2016 (EP) .................................... 16163171

(51) Int. Cl.
*A61M 15/00* (2006.01)

(52) U.S. Cl.
CPC ...... *A61M 15/0021* (2014.02); *A61M 15/009* (2013.01); *A61M 15/0086* (2013.01); *A61M 2205/0238* (2013.01)

(58) Field of Classification Search
CPC .......... A61M 15/0021; A61M 15/0086; A61M 15/009; A61M 2205/0238; A61M 11/00; A61M 11/08; A61M 15/0001; A61M 15/0023; A61M 15/0025; A61M 15/0026
See application file for complete search history.

(56) References Cited

U.S. PATENT DOCUMENTS 3,236,458 A 2/1966 Ramis
3,980,074 A * 9/1976 Watt .................... A61B 5/0813 128/203.15
3,994,421 A 11/1976 Hansen
5,115,803 A 5/1992 Sioutas
5,899,201 A * 5/1999 Schultz ............ A61M 15/0086 128/200.14

(Continued)

FOREIGN PATENT DOCUMENTS

DE 26 42 174 4/1977
EP 0 412 648 2/1991

(Continued)

OTHER PUBLICATIONS

International Search Report in Application No. PCT/EP2017/057293 dated Jun. 21, 2017.

(Continued)

*Primary Examiner* — Tu A Vo
(74) *Attorney, Agent, or Firm* — Oblon, McClelland, Maier & Neustadt, L.L.P.

(57) ABSTRACT

An actuator for a pressurized metered dose inhaler providing a significant reduction in the non-respirable coarse fraction of the emitted aerosol medicament impacting in the oro-pharynx, with consequent less associated side effects and oral candidiasis in the patient, due to the fact that the mouthpiece portion has a central rounded opening of a well-defined width and distance from the nozzle aperture and also provided with a cylindrical recess, whose central axis is aligned with the central longitudinal axis of the mouthpiece portion and with the central longitudinal axis of the nozzle channel.

19 Claims, 4 Drawing Sheets

(56) References Cited

U.S. PATENT DOCUMENTS

| | | | | |
|---|---|---|---|---|
| 2003/0041859 A1* | 3/2003 | Abrams | ............... | A61M 16/101 |
| | | | | 128/200.22 |
| 2005/0268915 A1* | 12/2005 | Wassenaar | ............ | A61M 15/08 |
| | | | | 128/206.11 |
| 2006/0269484 A1* | 11/2006 | Knopeck | ................. | A61P 11/06 |
| | | | | 424/45 |
| 2009/0020114 A1* | 1/2009 | Brambilla | ............... | A61P 11/06 |
| | | | | 128/200.23 |
| 2011/0011394 A1* | 1/2011 | Edwards | ................ | A23G 1/305 |
| | | | | 128/200.18 |
| 2014/0190478 A1* | 7/2014 | Liu | ........................ | A24F 47/008 |
| | | | | 128/202.21 |
| 2014/0305429 A1* | 10/2014 | Lewis | ............... | A61M 15/0003 |
| | | | | 128/200.19 |
| 2016/0325058 A1* | 11/2016 | Samson | ................. | A61B 5/087 |

FOREIGN PATENT DOCUMENTS

| | | | | |
|---|---|---|---|---|
| EP | 0 546 009 | | 6/1993 | |
| WO | 94/27663 | | 12/1994 | |
| WO | 00/50112 | | 8/2000 | |
| WO | WO-2014046993 A1 * | 3/2014 | .......... | A61M 11/002 |

OTHER PUBLICATIONS

European Search Report in Application No. 16163171 dated Jun. 6, 2016.

\* cited by examiner

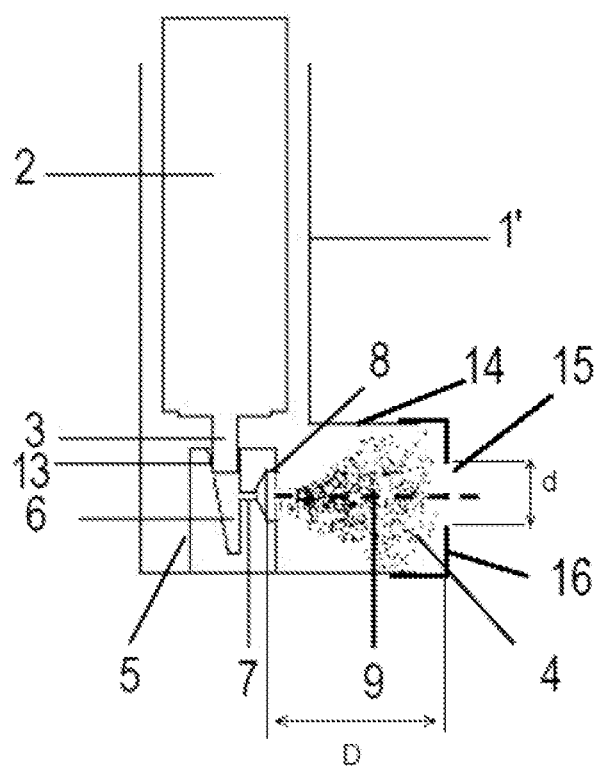
Fig. 2a
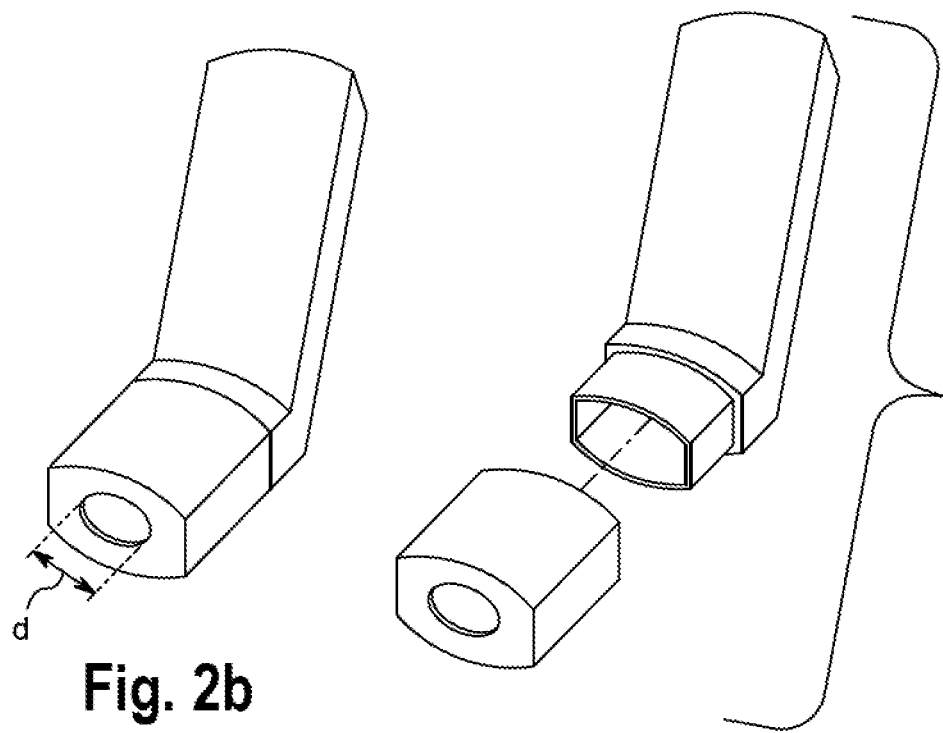
Fig. 2b
Fig. 2c

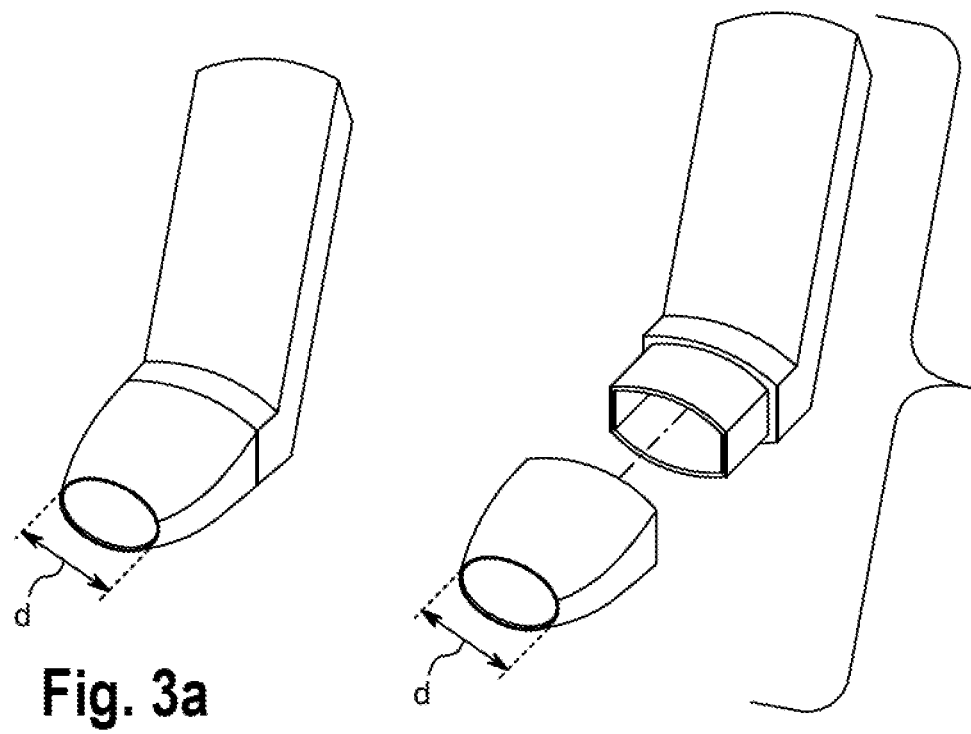
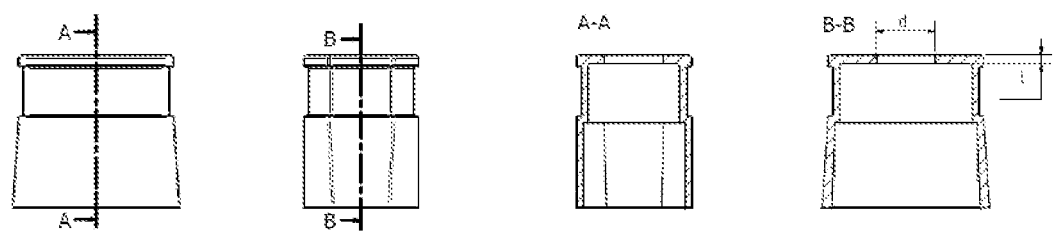
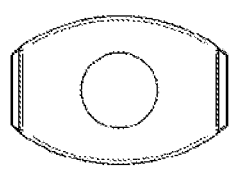 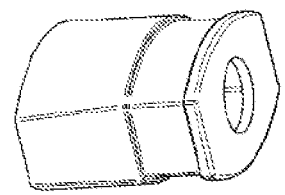
Fig. 4e      Fig. 4f

AEROSOL INHALATION DEVICE

CROSS REFERENCES TO RELATED APPLICATIONS

This application claims priority to European Patent Application No. 16163171.8, filed on Mar. 31, 2016, which is incorporated herein by reference in its entirety.

BACKGROUND OF THE INVENTION

Field of the Invention

The present invention relates to inhalers for medicaments and, in particular, to improved aerosol devices for transferring to the respiratory system of a patient, mainly to the lungs, by oral inhalation, a metered dose of a medicament contained in a pressurized dispensing container. The present invention also relates to methods of treating certain diseases and conditions by administering a medicament to a subject in need thereof by such an inhaler.

Discussion of the Background

The use of aerosol inhalation devices for the delivery by inhalation of medicaments in form of aerosol is well known. Among the devices available to deliver medicaments to the lungs, pressurised metered-dose inhalers (pMDIs) are widely used.

pMDIs are aerosol delivery systems designed to deliver one or more medicaments formulated with a pressure liquefied propellant gas or propellant gas mixture and optional additives or excipients.

pMDIs are designed to meter a predetermined amount of the medicament, completely dissolved (in solution) or in form of micronized solid particles dispersed or suspended in the formulation, and to dispense the dose as an inhalable aerosol cloud upon actuation.

A conventional pMDI is shown in FIGS. 1a and 1b. The pMDI comprises an actuator 1 comprising, in its vertical hollow portion, a housing adapted to receive a canister 2. The canister 2 contains an aerosol formulation wherein one or more medicaments are in solution or are dispersed in suspension in a pressure liquified low boiling point propellant system optionally comprising suitable pharmaceutically acceptable additives or excipients. The canister 2 is normally provided with a metering valve, having a hollow valve stem 3, for measuring and releasing discrete doses of the medicament formulation on each actuation. The dose is dispensed as an inhalable aerosol cloud or plume 4.

Typical actuators 1 have a nozzle assembly or nozzle block 5, which receives the hollow valve stem 3 of the aerosol canister 2. The nozzle block 5 defines the walls of the valve stem receptacle 13, an expansion chamber 6 (also defined as sump), and a nozzle channel 7 which ends in an aperture 8 having an enlarging frusto-conical section.

The nozzle channel 7 through its aperture 8 serves to propel the aerosol formulation into the mouthpiece portion 14, towards a mouthpiece opening 10 for the delivery of the aerosol formulation. Traditionally, the nozzle channel 7 has been provided such that its longitudinal axis is aligned with a longitudinal axis 9 of the actuator mouthpiece portion 14, so that the aerosol exits the channel in a mean direction towards a mouthpiece opening 10. The longitudinal axis of the nozzle channel 7 in the nozzle block 5, aligned with the longitudinal axis 9 of the mouthpiece portion 14 as above reported, is normally located at an angle greater or equal to 90°, preferably in the range from approximately 90° to approximately 120°, and more preferably from approximately 90° to approximately 110° to the direction of the longitudinal axis of the hollow valve stem 3 of the aerosol canister 2. Therefore, when the canister 2 is actuated, the formulation containing the propellant moves down the stem 3 and expands within the expansion chamber 6 before being propelled through the nozzle channel 7 from its opening 8 towards the mouthpiece opening 10. The formulation, therefore, is atomized in a direction extending at an angle greater or equal to 90°, preferably in the range from approximately 90° to approximately 120°, and more preferably from approximately 90° to approximately 110° with respect to the longitudinal axis of the aerosol canister 2.

Typically in the known pMDIs marketed a protective mouthpiece cover or dust cap 11 is present to keep close the mouthpiece opening 10 when the pMDI is not used.

In known pMDIs the medicament is discharged in response to the user's actuation, performed by depressing the base of the canister relative to the valve stem engaged in the nozzle block of the actuator. At the same time, the medicament is inhaled through the mouthpiece opening by the user that, during the inspiration act, creates an airflow entering from the spaces between the external walls of the canister 2 and the internal walls of the vertical portion of the actuator 1, located upstream from the mouthpiece portion.

Typically in such devices, there is little or no restriction in the airflow between the entering air and the mouthpiece portion. Because of this, a substantial airflow may be created by a user of the device upon inspiration and, because the medicament is fired into the airflow in the same direction as the airflow, the effect is that emitted medicament particles can be travelling at quite substantial velocities, e.g. in excess of 40 m/s, when they reach the mouthpiece. As inhalers of this type are normally designed to be as small as practical for the convenience of users, the distance between the point at which the medicament is fired into the airflow and the patient's mouth is usually quite small (about from 25 to 30 mm) so that there is little distance to reduce the inertia of the particles of medicament. This results in that coarse, non-respirable (>9 μm aerodynamic diameter) aerosol particles may impact and deposit on the mouth, throat and pharynx walls.

This is normally undesirable, since the medicament is designed for delivery to the respiratory system and may not have an appropriate effect when deposited in the mouth and throat. In addition, it may potentially cause oral candidiasis and dysphonia and systemic side effects, when allowed to enter the digestive tract by swallowing.

These effects can currently be prevented by the use of add-on devices, spacers or holding chambers such as the Volumatic® and AeroChamber Plus®, which are able to prevent a large proportion of the coarse particles from the dose of the aerosol depositing in the patient's oro-pharynx and being swallowed.

Various attempts have been made to modify the spray characteristics of inhalers. GB-A-2279879, EP-A-412648 and EP-A-0839544, which are incorporated herein by reference in their entireties, disclose inhalers in which air inlets and/or a frustoconical diverter with a small orifice are arranged in the mouthpiece portion such that during inhalation a turbulent airflow is created which may decelerate the aerosol particles to be inhaled while the propellant is mainly diverted out of the device.

EP-A-862921, which is incorporated herein by reference in its entirety, discloses similar devices comprising also a flow controller manually depressible to unseal the air inlets.

WO 93/05837 and U.S. Pat. No. 4,972,830, which are incorporated herein by reference in their entireties, disclose inhalers in which the passage which directs the pressurized medicament from the canister to the chamber has particular configurations to reduce the velocity of the spray and enhance dispersion of the medicament in the airflow. WO 94/27663 and WO 00/50112, which are incorporated herein by reference in their entireties, relate to actuators arranged to try to reduce the velocity of the spray exiting the mouthpiece such that more drug may reach the lower airways.

An analogous principle has been followed in three patent applications directed to very similar devices: WO 2008/023014, which is incorporated herein by reference in its entirety, wherein the actuator outlet, through which the user inhales, has a substantially closed rear end section which partitions the outlet from the housing such that, on inhalation, an air flow is drawn substantially from an outer peripheral surface of the outlet; WO 2008/023015, which is incorporated herein by reference in its entirety, wherein the outlet includes at least one flow path which provides for a substantially annular air flow as to provide a sheathing air flow; and WO 2008/023018, which is incorporated herein by reference in its entirety, wherein the nozzle outlet, coupled or integrally formed with the actuator outlet, is present as a separately-formed component from the nozzle block and may be provided with one or more air inlets of different shapes positioned around the orifice outlet of the nozzle block.

However, in these cases the drug delivery characteristics such as the respirable dose, also defined as the Fine Particle Dose (FPD), which is the amount of aerosol particles with aerodynamic diameter less or equal to 5 µm, and the Particle Size Distribution (PSD), which is the relative amount, by mass, of particles according to specific ranges of sizes of the emitted aerosol, are not considered identical to those of a conventional pMDI product. In addition, some of these devices are also bulky and inconvenient for the patients to carry on with them, often leading to a reduction in patient compliance.

In view of the above, there is a continued need for such actuators and metered-dose inhalers which allow a substantial fraction of non-respirable particles or droplets to be removed from the aerosol cloud before it is dispensed through a mouthpiece opening without affecting negatively other parameters of the emitted aerosol, mainly the respirable dose, or FPD, without increasing the size or significantly altering the shape of the inhaler.

In the same time, during the use, it is also important to avoid or to minimize the risk that the coarse, non respirable particles of medicament, retained in a such actuator after cumulative administrations, may escape from the actuator in form of high spots reaching the patient mouth or oropharynx. These high spots, in fact, may contain high amounts of medicament that, on swallowing, may cause potential safety risk to patients. Thus, there remains a need for improved aerosol inhalers.

SUMMARY OF THE INVENTION

Accordingly, it is one object of the present invention to provide novel actuators and metered-dose inhalers.

It is another object of the present invention to provide novel actuators and metered-dose inhalers which allow a substantial fraction of non-respirable particles or droplets to be removed from an aerosol cloud before the aerosol cloud is dispensed through a mouthpiece opening without affecting negatively the parameters of the emitted aerosol, such as the respirable dose, or fine particle dose (FPD) without increasing the size or significantly altering the shape of the inhaler.

It is another object of the present invention to provide novel methods of treating certain diseases and conditions by administering a medicament to subject in need thereof by such an inhaler.

These and other objects, which will become apparent during the following detailed description, have been achieved by the inventors' discovery of an actuator for an aerosol inhalation device comprising:

(a) a housing adapted to receive an aerosol canister containing a pressurized medicament formulation, provided with a metering valve having a hollow valve stem;

(b) a nozzle block defining a valve stem receptacle, an expansion chamber or sump, a nozzle channel, and an aperture to propel the aerosol formulation towards the mouthpiece opening; and (c) a mouthpiece portion, having a central longitudinal axis located at an angle greater or equal to 90° to the direction of the longitudinal axis of the hollow valve stem, terminating in a mouthpiece opening through which the user inhales, characterized in that said mouthpiece portion comprises a central rounded opening of a surface corresponding to the surface of a circular shaped opening of a diameter d from 5 to 14 mm and at a distance D from 16 to 58 mm from the nozzle channel external aperture and whose central axis is aligned with the central longitudinal axis of the actuator mouthpiece portion and substantially coinciding with the central longitudinal axis of the nozzle channel.

In particular, said central rounded opening of the mouthpiece reduces the width of a typical mouthpiece opening of a conventional pMDI, normally totally opened, as being defined by the lateral walls of the mouthpiece portion of the actuator (FIG. 1b).

In a preferred embodiment said central rounded opening has a circular shape but in an alternative embodiment it could also have an elliptical or ovoidal shape provided they have the same surfaces.

The central opening is configured on a planar surface normal to the lateral walls of the mouthpiece portion.

In a further alternative embodiment the central opening is located on a convex, rounded frustoconical restriction of the walls of the mouthpiece portion.

The thickness of the central opening is defined by the conventional thickness of the walls of the mouthpiece portion of a pMDI.

In an alternative embodiment the profile of the central rounded opening may have an edge facing towards the inside of the mouthpiece and wherein the internal extension of the edge may form a recess at an angle of any value in the range from 30° to 150° with respect to the plane of the wall defining the said central opening, and therefore the recess may have a cylindrical or frustoconical shape.

According to another aspect the invention provides a tubular element having an opening of suitable shape and dimensions to be securely snapped into place with the external mouthpiece of a conventional actuator of the prior art and the opposite opening provided with a mouthpiece portion with a central rounded opening of the said defined width and distance from the nozzle channel external aperture as described above for the actuator according to the invention. The said tubular element may be formed of the same material as the conventional actuator or of a different material specifically suited to its purposes.

In an additional preferred embodiment the parts of the internal wall of the mouthpiece portion, surrounding the mouthpiece opening of reduced width, is coated or embedded by an absorbing or entrapping material to avoid the release in the inhalation flow of the coarse particles of the aerosol which impact on or may adhere to the internal surfaces of the mouthpiece portion.

The absorbing or entrapping material may be constituted by one or more layers of a natural or synthetic, porous or filtering material which may be preferably selected from sintered glass or porcelain, paper, foam, sponge, a polymeric, a plastic or a metal grid of suitable shape, weave and mesh or any other suitable filtering material.

The one or more layers of absorbing or entrapping material of suitable dimension may be fixed to the internal walls of the mouthpiece, surrounding the mouthpiece opening, by using any suitable mechanical, physical or chemical joining procedure such as interlocking, snapping, welding, soldering or other suitable techniques such as by a chemical bonding process among which adhesive bonding.

In an alternative embodiment, the surface of the portion of the internal wall of the mouthpiece, surrounding the mouthpiece opening, may present different alternative surface textures or coatings, in fact it may be smooth or wrinkled, with different degrees of roughness, to optimise the performance of the device.

The central rounded opening width of the present actuator with circular shape is defined by its internal diameter d which is from 5 to 14 mm, preferably from 8 to 12 mm, even more preferably from 9 to 12 mm and the particularly preferred diameter is selected from about 9, 10, 11, and 12 mm.

The central rounded opening width of the present actuator with ellipsoidal or ovoidal shape is defined by its respective area, corresponding to the area of the circular shaped opening with the diameter in the range as described above. In particular, the corresponding area is from 20 to 154 mm$^2$, preferably from 50 to 113 mm$^2$, even more preferably from 64 to 113 mm$^2$, and the particularly preferred area is selected from about 64, 79, 95, and 113 mm$^2$.

The central rounded opening has a distance D from the nozzle channel external aperture from 16 to 58 mm, preferably from 28.5 to 58 mm, even more preferably from 38.5 to 54.1 mm, and the particularly preferred distance is selected from about 38.5, 41.0, 45.0, 50.3, and 54.1 mm.

The actuator of the invention is also defined by the optimal ratio d/D between the internal diameter of the central rounded opening of the mouthpiece portion (in mm) and its distance from the nozzle channel external aperture (in mm). Said ratio d/D is in the range from 0.09 to 0.88, preferably from 0.14 to 0.42, more preferably from 0.17 to 0.31, and the particularly preferred ratio is selected from about 0.20, 0.22, 0.23, 0.24, 0.26, 0.27 and 0.28.

The walls of the mouthpiece portion may have a conventional thickness for this kind of devices known to the skilled in the art, however, suitable thickness may be from 0.1 to 3 mm or more, preferably from 0.2 to 2 mm, more preferably from 0.8 to 1.8 mm and most preferably of 1 or 1.5 mm.

In an alternative embodiment, wherein the profile of the central rounded opening has an edge facing towards the inside of the mouthpiece, said edge forms a recess at an angle of any value in the range from 30° to 150° with respect to the plane of the wall defining the said central rounded opening, preferably said angle is in the range from 45° to 135°, even more preferably from 80° to 120° and the most preferred is 90°±2° and in particular it is selected from 88°, 89°, 90°, 91°, and 92°. In a further alternative, the angle of the edge with respect to the plane of the wall defining the said central opening may be of 90° and may have the shape of a cylindrical recess.

The said edge, facing towards the inside of the mouthpiece forms a recess having a length t from 2 to 15 mm, preferably from 4 to 10 mm and, even more preferably, the length t is selected among 4, 5, and 6 mm and the recess is cylindrical.

According to another aspect, the present invention provides an inhaler comprising an aerosol canister, containing a pressurised medicament formulation, having a metering valve and a valve stem to be fitted into the valve stem receptacle of an actuator of any one aspect or embodiment described herein or of a conventional actuator provided with a tubular element with a mouthpiece portion of any one aspect or embodiment described herein.

The most preferred embodiment is a tubular element having an opening of suitable shape and dimensions to be securely snapped into place with the external mouthpiece of a conventional actuator of the prior art and the opposite opening provided with a mouthpiece portion characterised in that it comprises:

a central circular opening of an internal diameter d which is selected from about 9, 10, 11, and 12 mm, at a distance D selected from about 38.5, 41.0, 45.0, 50.3, and 54.1 mm from the nozzle channel external aperture, whose central axis is aligned with the central longitudinal axis of the actuator mouthpiece portion and substantially coinciding with the central longitudinal axis of the nozzle channel, wherein the profile of the central circular opening has an edge facing towards the inside of the mouthpiece, forming a cylindrical recess at an angle of 90° with respect to the plane of the wall defining the said central opening for a length t from 4 to 10 mm, and in particular the length t is selected among 4, 5, and 6 mm.

According to a further aspect the present invention provides a kit of parts comprising an actuator of an aerosol inhalation device and the optimised tubular element with suitable shape and dimensions which is securely snapped into place with the external mouthpiece portion of the actuator and an aerosol canister containing a pressurised medicament formulation.

According to another aspect, the present invention provides a method in which an actuator of any one aspect or embodiment described herein is used for the reduction of the non-respirable dose and consequent potential oro-pharyngeal deposition of the dispensed aerosol formulation on actuation of a metered-dose inhaler. The said method may be used to dispense the aerosol formulation without interaction with a human or animal body. The method may, for example, be used to dispense an aerosol formulation when priming a metered dose inhaler.

Another aspect of the present invention is the use of an actuator with a mouthpiece portion comprising a central rounded opening of a defined width and distance according to any aspect or embodiment described herein for the reduction of the non-respirable dose and consequent potential oro-pharyngeal deposition of the dispensed aerosol formulation on actuation of the inhaler.

The presence of a central rounded opening of a defined width and distance according to the present invention manipulates the airflow internal to the mouthpiece, permitting to intercept into the actuator the external droplets of the emitted aerosol plume generating coarser aerosol particles while the droplets more internal to the plume, generating fine aerosol particles, freely exit the actuator through the reduced rounded mouthpiece opening.

Among the main advantages over conventional inhalers is a noteworthy and significant reduction of at least 50% by weight, but in certain embodiments up to 70 or 80% by weight, of the non-respirable coarse fraction of the emitted aerosol medicament via inertial impaction and retention inside the actuator rather than in the oro-pharynx. Non-respirable fraction is often associated with systemic side effects and oral candidiasis and dysphonia (in case of inhaled corticosteroid treatment) in the patient.

In addition, the presence of a said central reduced rounded opening has minimal, negligible impact on the particle size distribution (PSD) of the delivered particles having aerodynamic diameter lower than 9 μm. In fact, the PSD observed in vitro using the Next Generation Impactor (NGI) fitted with an induction port (Apparatus E, European Pharmacopoeia $8^{th}$ Ed. Suppl 8.5, 2014, which is incorporated herein by reference in its entirety) is extremely comparable with that of a conventional actuator.

An actuator according to the present invention, retaining the coarse fraction of the emitted dose in the actuator via inertial impaction, may remove the requirement for add-on devices, spacers or holding chambers such as the Volumatic® and AeroChamber Plus®, which prevent a large proportion of the coarse particles from the dose reaching the patient, but produce dramatically changes in the PSD with respect to "actuator only" products. This reduces the need to carry such add-on devices which are cumbersome and is an additional factor considering patient compliance.

This kind of actuator is compatible with the pMDI aerosol formulation technology based on hydrofluoroalkane (HFA) propellants. The aerosol formulation may be an aerosol solution formulation or an aerosol suspension formulation wherein the at least one active ingredient is respectively completely dissolved in a propellant or in a propellant-solvent mixture or dispersed in form of solid micronized particles in a propellant or in a propellant mixture. This kind of actuator is particularly effective when used with pMDI aerosol solution formulations. The aerosol formulation may contain at least one active ingredient in a propellant or in a propellant-solvent system and, optionally, further excipients. In particular with solution formulation comprising an alcohol an optional low volatility component such as, for example glycerol or a glycol may be present.

The performance of this kind of actuator through-can-life is consistent.

Any possible deposit of the medicament in the actuator of the invention and in particular in the mouthpiece portion of the actuator may be removed through conventional washing or cleaning techniques. In these cases, the availability of the embodiment wherein the central rounded opening is provided on an optimised tubular element with suitable shape and dimensions which is snapped into place with the external mouthpiece portion of the actuator is particularly advantageous, permitting the removal of the tubular element and better cleaning of the mouthpiece portion.

The actuator cleaning procedures may be avoided or minimized in the case of the embodiment wherein the internal walls of the mouthpiece portion surrounding the mouthpiece opening is coated or provided with an absorbing or entrapping porous material.

It has been also demonstrated that a further advantage of a preferred embodiment of the invention, wherein the profile of the central rounded opening of the mouthpiece portion has an edge facing towards the inside of the mouthpiece, forming a recess of selected length and angle with respect to the plane of the wall defining the said central rounded opening, is that during the patient use of the device, the coarse particles of the medicament doses sprayed, after cumulative administrations, are retained into the actuator and do not escape in form of high spots containing high amounts of active ingredients which may cause potential safety risk to patients if swallowed.

The improvement of the patient compliance through the reduction of the spray force is another advantage of the invention. The spray force is linked, in fact, to the so-called cold freon effect, the sensation due to the high velocity blast and subsequent evaporation of the liquid propellant in droplets that impact on the patient throat causing cough, irritation or discomfort and reduction in the patient coordination between the actuation of the inhaler and the inhalatory act.

The improved actuator according to the invention has no effect on the internal resistance of the device to the inhalatory act.

To improve the patient's coordination, the actuator according to the present invention may be also provided with an add-on optical or acoustic signaling device advising the patient when an effective inhalation flow is reached.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 2a is a schematic lateral cross-sectional view of a pMDI actuator of an embodiment of the present invention.

FIGS. 2b and 2c represent schematic prospective dews of a pMDI actuator of an embodiment of the present invention wherein the central rounded opening of the mouthpiece has a circular shape and wherein the circular shaped mouthpiece opening is provided on a tubular element shown both detached (FIG. 2c, on the right) or securely snapped into place (FIG. 2b, on the left) over the external mouthpiece portion of a conventional actuator 1 of FIG. 1.

FIGS. 3a and 3b are schematic prospective views of a pMDI actuator of an embodiment of the present invention (single piece FIG. 3a, on the left; in two pieces FIG. 3h, on the right) having a circular shaped central mouthpiece opening located on a convex, rounded, frustoconical restriction of the walls of the mouthpiece portion.

FIGS. 4a to 4f are schematic different views of an embodiment of the present invention wherein a circular shaped mouthpiece opening is provided on a tubular element to be securely snapped into place with the external mouthpiece portion of the actuator.

DETAILED DESCRIPTION OF THE PREFERRED EMBODIMENTS

Figure 1A:
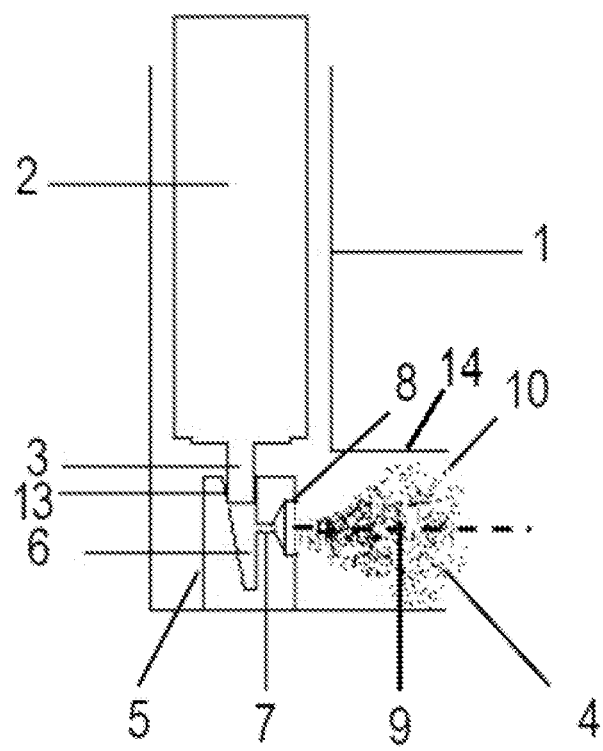
FIG. 1a is a schematic lateral cross-sectional view of a conventional pressurized metered dose inhaler (pMDI) according to the prior art wherein the mouthpiece opening is completely opened and has no restrictions.

The terms "active drug," "active ingredient," "active," "active compound", "active substance," "medicament," and "therapeutic agent" are used synonymously. 'The terms "nozzle block" or "nozzle assembly" are synonyms to define an almost cylindrical element, which accommodates the valve stem of the aerosol canister and directs the emitted dose towards the mouthpiece. It rigidly extends in the actuator housing adapted to receive the canister from a central internal position of its base.

The term "aligned" when referring to two axes means "coinciding or parallel to each other". By "substantially aligned with" it is meant that the axes deviate by less 30°, preferably less than 15°, more preferably less than 5°, even more preferably less than 3°, even more preferably less than 2°, even more preferably less than 1°.

By "substantially coinciding with" it is meant that the axes deviate by less 30°, preferably less than 15°, more preferably less than 5°, even more preferably less than 3°, even more preferably less than 2°, even more preferably less than 1°, and that the axes are offset by no more than 10 mm, preferably no more than 5 mm, more preferably no more than 2 mm, even more preferably no more than 1 mm, even more preferably no more than 0.5 mm, even more preferably no more than 0.1 mm.

The term "longitudinal axis" refers to a center longitudinal axis of the respective concavity of component.

"Respirable fraction" also defined as "fine particle fraction" refers to an index of the percentage of active particles which would reach the deep lungs in a patient.

The respirable fraction is calculated by the ratio between the "respirable dose" and the "delivered dose." They are evaluated in vitro using a Next Generation Impactor (NGI) fitted with an induction port (Apparatus E, European Pharmacopoeia $8^{th}$ Ed. Suppl 8.5, 2014, which is incorporated herein by reference in its entirety).

The "delivered dose" is determined from the cumulative deposition in the apparatus, while the "respirable dose," also defined as "Fine Particle Dose" (FPD) is calculated as the amount of particles with aerodynamic diameter less or equal to 5 μm.

The "extra-fine particle dose" (eFPD) is etermined as the amount of particles with aerodynamic diameter less or equal to 1 μm.

The "non-respirable" dose is the amount of larger aerosol particles that, upon inhalation, impact within the mouth and throat of the patient and may be swallowed, potentially causing side effects. It is mainly determined by the amount of the emitted aerosol particles blocked at the level of the induction port.

Exemplary embodiments of the invention will now be described with reference to the drawings. The features of the embodiments may be combined with each other unless specifically stated otherwise.

FIG. 2a is a schematic lateral cross-sectional view taken along the center symmetry plane, of an actuator 1' for a pMDI inhaler according to the present invention comprising, in its vertical hollow portion, a housing adapted to receive a canister 2. The canister 2 contains an aerosol formulation wherein one or more medicament is in solution or in suspension in a pressure liquified low boiling point propellant system optionally comprising at least one suitable pharmaceutically acceptable additive. The canister 2 may be configured as a conventional canister for a pMDI, provided with a metering valve and a hollow valve stem 3. The metering valve, allows a metered dose of the medicament formulation to be dispensed through the hollow valve stem 3 on each actuation.

The actuator 1' includes a nozzle assembly or nozzle block 5, which may be integrally formed with the housing of the actuator. The nozzle block 5 defines the walls of the valve stem receptacle 13, an expansion chamber or sump 6, and a nozzle channel 7, which ends in an aperture 8, having an enlarging frusto-conical section. The nozzle channel 7 has been provided such that its longitudinal axis is aligned with a longitudinal axis 9 of the actuator mouthpiece portion 14, so that the aerosol cloud 4 exits the channel in a mean direction towards its opening 15.

The mouthpiece portion 14 central longitudinal axis 9, aligned with the longitudinal axis of the nozzle channel 7, is located at an angle greater or equal to 90° to the direction of the longitudinal axis of the hollow valve stem 3 of the aerosol canister 2 and terminates in a mouthpiece opening 15, through which the user inhales.

The angle between the longitudinal axis 9 of the mouthpiece portion 14 and the longitudinal axis of the hollow valve stem 3 is preferably in the range from approximately 90° to approximately 120°, and more preferably from approximately 90° to approximately 110°.

The mouthpiece portion 14, terminating in a mouthpiece through which the user inhales, comprises a central rounded opening 15 of a defined width and distance D from the nozzle channel external aperture 8 and whose central axis is aligned with the central longitudinal axis 9 of the actuator mouthpiece portion 14, substantially coinciding with the central longitudinal axis of the nozzle channel 7.

Figure 1B:
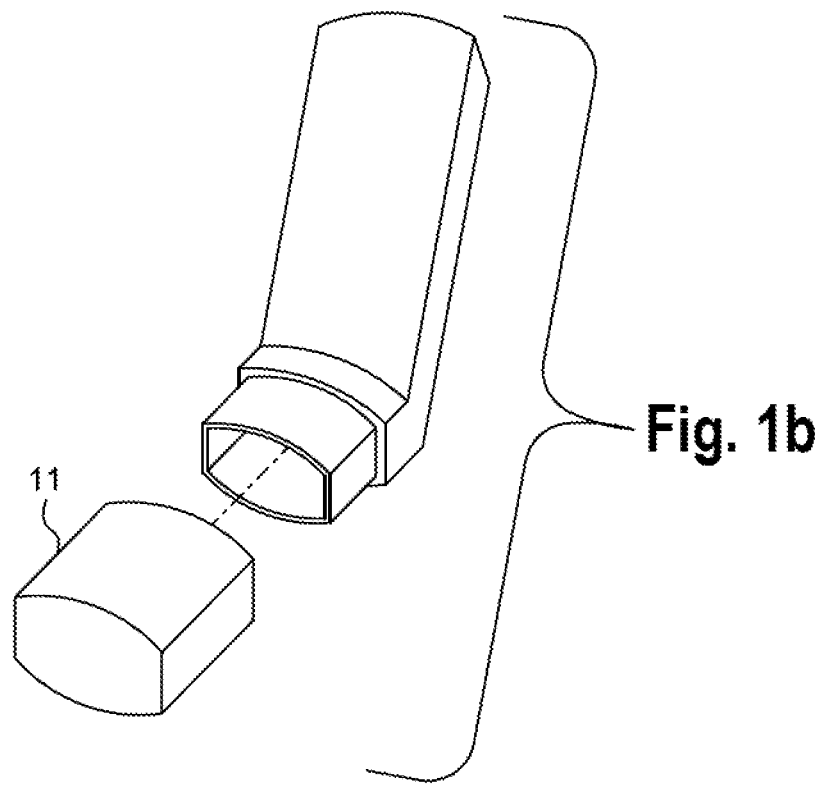
FIG. 1b is a schematic prospective view of a conventional pMDI according to the prior art.

The said central rounded opening 15 has a reduced width with respect to a typical mouthpiece 10 of a conventional pMDI actuator 1 as shown in FIG. 1, which is normally totally opened (as being defined by the parallel lateral walls of the mouthpiece portion of the actuator).

The central rounded opening 15 is configured on a planar surface 16 normal to the lateral walls of the mouthpiece portion 14 and has a shape that could be selected from circular, elliptical and ovoidal shape but the circular shape, as shown in FIG. 2b is preferred.

In an alternative embodiment as shown in the actuator of FIGS. 3a and 3b, the central opening is located on a convex, rounded frustoconical restriction of the walls of the mouthpiece portion.

The width of the central rounded opening 15 of the actuator with circular shape is defined by its internal diameter d of the opening. The said diameter is selected in the range which is from 5 to 14 mm, preferably from 8 to 12 mm, even more preferably from 9 to 12 mm and the particularly preferred diameter is selected from about 9, 10, 11, and 12 mm.

In this case, manufacturing tolerances of from ±0.3 to ±0.1 mm are acceptable and are also included in the present invention.

The width of central rounded opening 15 of the actuator with ellipsoidal or ovoidal shape is defined by its respective area, corresponding to the area of the circular shape opening with the diameter selected in the range as described above. In particular, the corresponding area is from 20 to 153 mm$^2$, preferably from 50 to 113 mm$^2$, even more preferably from 64 to 113 mm$^2$, and the particularly preferred area is selected from about 64, 79, 95 and 113 mm$^2$.

The central rounded opening 15 has a distance D from the nozzle channel external aperture 8 which is from 16 to 58 mm, preferably from 28.5 to 58 mm, even more preferably from 38.5 to 54.1 mm, and the particularly preferred length is selected from about 38.5, 41.0, 50.3, and 54.1 mm. In this case, manufacturing tolerances of from ±0.5 to ±0.0.2 mm are acceptable and are also included in the invention.

FIGS. 4a to 4f are schematic different views of an embodiment of the present invention wherein a circular shaped mouthpiece opening is provided on a tubular element to be securely snapped into place with the external mouthpiece portion of a conventional actuator 1 of FIG. 1 as shown in FIGS. 2a and 2b.

FIG. 4a and FIG. 4b represent respectively an upper and a lateral view of the tubular element having the circular shaped mouthpiece opening according to the invention.

FIG. 4c and FIG. 4d represent, respectively, section views of FIG. 4a on the plane A-A, and FIG. 4b on the plane B-B.

FIG. 4e is a front view from the side of the circular mouthpiece opening and FIG. 4f is a schematic perspective view of the tubular element. As shown in the figures, one side of said tubular member is provided with a circular shaped mouthpiece opening 15 of diameter d according to the invention (FIG. 4e). The other side of said tubular member, opposite to the mouthpiece opening, is provided with an opening with suitable shape and dimensions as to be fitted and to be securely snapped into place over the external mouthpiece portion 14 of an actuator 1 as shown in FIGS. 2a and 2b so that the distance D between the circular mouthpiece opening 15 and the nozzle channel external aperture 8 is maintained the same as above described.

In an alternative embodiment the other side of said tubular member, opposite to the circular mouthpiece opening, is provided with an opening with suitable shape and dimensions as to be fitted and to be securely snapped into place internally to the mouthpiece portion 14 of the actuator 1 of FIG. 1.

The thickness t of the wall 16 defining the central opening 15 of the actuator mouthpiece according to the invention as shown in FIG. 2a is defined by the conventional thickness of the walls of the mouthpiece portion for a pMDI device, well known to the skilled in the art. However, as shown for instance in FIG. 4d, a suitable thickness t of the wall defining the central opening may be from 0.1 to 3 mm or more, preferably from 0.2 to 2 mm, more preferably from 0.8 to 1.8 mm and most preferably of 1 or 1.5 mm. In this case, manufacturing tolerances of from ±0.05 to ±0.2 mm are acceptable and are also included in the present invention.

Figure 5G:
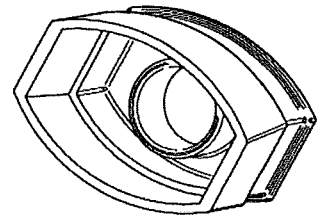
Figure 6:
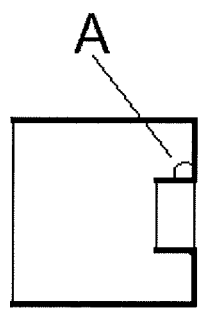
FIG. 6 is a schematic lateral cross-sectional view of a tubular element wherein the profile of the central opening has the edge facing towards the inside of the mouthpiece and wherein the extension of the edge forms an angle A of 90° with respect to the plane of the wall defining the central opening.

In an alternative embodiment, as schematically shown in FIG. 6, the profile of the central circular opening has the edge facing towards the inside of the mouthpiece portion with an internal extension of the edge forming an angle A of 90° with respect to the plane of the wall defining the central opening. In alternative embodiments, the angle A may be selected in the range from 30° to 150°, preferably from 45° to 135°, even more preferably from 80° to 120° and the most preferred is 90°±2° and in particular it is selected from 88°, 89°, 90°, 91°, and 92°. The said internal extension of the edge may have the shape of a cylindrical recess when the angle A=90°, as shown also in a schematic perspective view in FIG. 5g, or the shape of a truncated cone whose larger base and smaller base may represent the mouthpiece opening when the angle is, respectively, 90°<A<150° and 30°<A<90°. In this case, manufacturing tolerances of ±2° are acceptable and are also included in the present invention.

FIGS. 5a to 5g are schematic different views of an alternative embodiment of the tubular element to be securely snapped into place with the external mouthpiece portion of the actuator and wherein the profile of the central opening has the edge facing towards the inside of the mouthpiece.

The extension of the edge forms an angle A of 90° with respect to the plane of the central opening, similarly to that of FIG. 6.

Figure 5A:
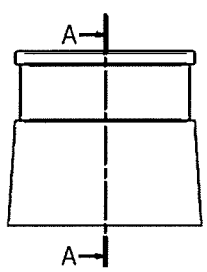
FIGS. 5a to 5g are schematic different views of an alternative embodiment of the tubular element to be securely snapped into place with the external mouthpiece portion of the actuator and wherein the profile of the central opening has the edge facing towards the inside of the mouthpiece, and this extension is normal to the plane of the central opening.
Figure 5B:
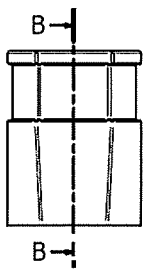

FIG. 5a and FIG. 5b represent respectively an upper and a lateral view of the tubular element.

Figure 5C:
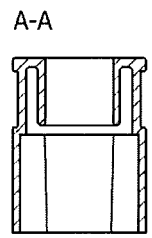
Figure 5D:
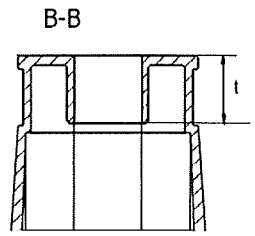

FIG. 5c and FIG. 5d represent, respectively, section views of FIG. 5a on the plane A-A, and FIG. 5b on the plane B-B.

Figure 5E:
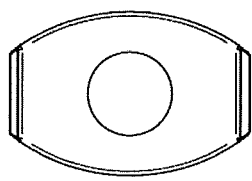
Figure 5F:
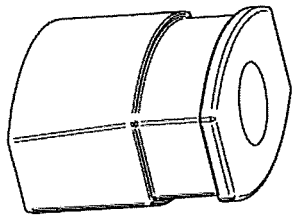

FIG. 5e is a front view from the side of the circular mouthpiece opening, FIG. 5f is a schematic perspective view of the tubular element and FIG. 5g is another schematic perspective view wherein is visible the cylindrical recess formed by the central opening edges, facing towards the inside of the mouthpiece.

The other side of said tubular member, opposite to the mouthpiece opening, and the thickness of its walls have the same features as those above described for the tubular element of FIGS. 4a to 4e.

In this case, however, as shown in FIG. 5d, the cylindrical recess formed by the central opening edges, facing towards the inside of the mouthpiece, has a length t from 2 to 15 mm, preferably 4 to 10 mm and even more preferably the length t is selected among 4, 5, and 6 mm.

In another embodiment, the tubular element provided with the central rounded opening of the invention to be snapped into place with the external mouthpiece portion of the actuator may be formed of the same material as the actuator or of a different material and may be molded as separate parts.

In a further alternative embodiment, the tubular element provided with the central rounded opening of the invention and the rest of the actuator may be molded in one piece, as a single unit, through single injection molding tools.

Examples of suitable materials for the actuator and or of the tubular element of the invention include metal materials such as aluminium, aluminium alloy or stainless steel; but also plastic polymeric materials, such as thermoplastic resins, optionally UV curable, including different grades of polypropylene (PP), the material of first choice in general for the pMDI actuators, but also polyethylene (PE), such as high density PE (HDPE); fluorinated polymers such as polytetrafluoroethylene (PTFE), fluorinated ethylene-propylene (FEP), perfluoroalkoxy alkane (PFA); acrylonitrile-butadiene-styrene (ABS); polyacrylate such as polymethyl methacrylate (PMMA); polycarbonate (PC); polyamide (PA, i.e. nylon); polyamideimide (PAI); polyimide (PI); polyesters such as polyethylene terephthalate (PET), polybutylene terephthalate (PBT); polysulfone (PS); polyarylsulfone (PAS); polyethersulfone (PES); and polydimethylsiloxane (PDMS).

Moreover the said plastic polymeric materials may be coated with antistatic agents by means of a molding or a coating process.

The pMDI devices are known. Said devices comprise a canister fitted with a metering valve. Part or the entire canister may be made of a metal, for example aluminium, aluminium alloy, stainless steel or anodized aluminium. Alternatively the canister may be a plastic can or a plastic-coated glass bottle.

The metal canisters may have part or all of their internal surfaces lined with an inert organic coating. Examples of preferred coatings are epoxy-phenol resins, perfluorinated polymers such as perfluoroalkoxyalkane, perfluoroalkoxyalkylene, perfluoroalkylenes such as poly-tetrafluoroethylene (Teflon), fluorinated-ethylene-propylene (FEP), polyether sulfone (PES) or fluorinated-ethylene-propylene polyether sulfone (FEP-PES) mixtures or combination thereof. Other suitable coatings could be polyamide, polyimide, polyamideimide, polyphenylene sulfide or their combinations.

Canisters having their internal surface lined with FEP-PES or Teflon may be used. Canisters made of stainless steel may also be used.

The canister is closed with a metering valve for delivering a therapeutically effective dose of the active ingredient. Generally the metering valve assembly comprises a ferrule having an aperture formed therein, a body molding attached to the ferrule which houses the metering chamber, a stem consisting of a core and a core extension, an inner- and an outer-seal around the metering chamber, a spring around the core, and a gasket to prevent leakage of propellant through the valve.

The gasket seal and the seals around the metering valve may comprise elastomeric material such as EPDM, chlorobutyl rubber, bromobutyl rubber, butyl rubber, or neoprene. EPDM rubbers are particularly preferred. The metering chamber, core and core extension are manufactured using suitable materials such as stainless steel, polyesters (e.g. polybutyleneterephthalate (PBT)), or acetals. The spring is manufactured from stainless steel eventually including titanium or other inert metal alloys. The ferrule may be made of a metal, for example aluminium, aluminium alloy, stainless steel or anodized aluminium. Suitable valves are available from manufacturers such as Valois, Bespak plc and 3M-Neotechnic Ltd.

The pMDI is actuated by a metering valve capable of delivering a volume of 25 to 100 µl preferably 40 to 70 µl and optionally 50 µl, or 63 µl per actuation.

In a typical arrangement, the valve stem is seated in a nozzle block communicating to an expansion chamber or sump. The expansion chamber has a nozzle channel terminating in an aperture which extends into the mouthpiece. Nozzle channels having a diameter in the range 0.15 to 0.45 mm and a length from 0.30 to 1.7 mm are generally suitable. Preferably, a nozzle channel having a diameter from 0.2 to 0.44 mm is used, and in particular nozzle channel diameter of 0.22, 0.25, 0.30, 0.33, or 0.42 mm is particularly preferred.

It may be useful to utilize actuators with nozzle channels having a diameter ranging from 0.10 to 0.22 mm, in particular from 0.12 to 0.18 mm, such as those described in WO 03/053501, which is incorporated herein by reference in its entirety. The use of said fine orifices may also increase the duration of the cloud generation and, hence, may facilitate the coordination of the cloud generation with the slow inspiration of the patient.

The canister contains an aerosol formulation which may be an aerosol solution formulation or an aerosol suspension formulation. The aerosol formulation may contain at least one active ingredient in a propellant or in a propellant/solvent system and, optionally, further pharmaceutical acceptable additive or excipient.

The at least one active ingredient of the formulation may be any known pharmaceutical active ingredient, administrable by inhalation alone or in combination for separate, sequential or simultaneous use. Preferably the active ingredient is known for prophylaxis or treatment of respiratory diseases and their symptoms, and in particular in diseases characterized by obstruction of the peripheral airways as a result of inflammation and presence of mucus, such as asthma of all types, chronic obstructive pulmonary disease (COPD), asthma-COPD overlap syndrome (ACOS), bronchiolitis, chronic bronchitis, emphysema, acute lung injury (ALI), cystic fibrosis, and adult or acute respiratory distress syndrome (ARDS).

The at least one active ingredient is selected from beta-2 agonists, inhaled corticosteroids, anti-muscarinic agents, phosphodiesterase IV inhibitors, dual muscarinic antagonist and beta-2-agonist, and combinations thereof.

More preferably the beta-2 agonist is selected from salbutamol, (R)-salbutamol (levalbuterol) fenoterol, formoterol (including the dihydrate), arformoterol, carmoterol (TA-2005), indacaterol, milveterol, vilanterol, olodaterol, abediterol, terbultaline, salmeterol, bitolterol, procaterol and metaproterenol in form of single stereoisomers, diastereoisomeric mixtures, and a pharmaceutically acceptable salt thereof or hydrate thereof.

More preferably the inhaled corticosteroid is selected from beclometasone dipropionate, fluticasone propionate, fluticasone furoate, butixocort, mometasone furoate, triamcinolone acetonide, budesonide and its 22R-epimer, ciclesonide, flunisolide, loteprednol, and rofleponide. More preferably the anti-muscarinic agent is selected from methscopolamine, ipratropium, oxitropium, tiotropium, glycopyrronium, aclidinium, umeclidinium, trospium and a salt thereof with a pharmaceutical acceptable counter ion.

More preferably the phosphodiesterase IV inhibitor is selected from cilomilast, piclomilast, roflumilast, tetomilast, CHF 6001, RPL 554 and a pharmaceutically acceptable salt thereof. Even more preferred active ingredients may be selected from beclometasone dipropionate, fluticasone propionate, fluticasone furoate, mometasone furoate and budesonide alone or in combination with one or more active ingredient selected from salbutamol, formoterol, salmeterol, indacaterol, vilanterol, glycopyrronium, tiotropium, aclidinium, umeclidinium and a salt thereof. The most preferred active ingredients are selected from beclometasone dipropionate, budesonide, formoterol fumarate (including the dihydrate), beclometasone dipropionate-salbutamol sulphate combination, beclometasone dipropionate-formoterol fumarate (including the dihydrate) combination and beclometasone dipropionate-formoterol fumarate (including the dihydrate)-glycopyrronium bromide combination.

The propellant may be any pressure-liquefied propellant and is preferably a hydrofluoroalkane (HFA), a hydrofluoroolefin (HFO) or a mixture of different HFAs or HFOs or, more preferably, it is selected from the group consisting of HFA 134a (1,1,1,2-tetrafluoroethane), HFA 227 (1,1,1,2,3,3,3-heptafluoropropane), and mixtures thereof.

The solvent which may be incorporated into the formulation has generally a higher polarity than that of the propellant and may include one or more substances selected from a pharmaceutically acceptable alcohol or a polyol.

Advantageously the solvent is selected from the group of lower branched or linear alkyl ($C_1$-$C_4$) alcohols such as ethanol and isopropyl alcohol. Preferably, the solvent is ethanol. It is preferred that the at least one pharmaceutically active ingredient of the formulation is substantially completely and homogeneously dissolved in the propellant/solvent, system, i.e. the composition is preferably a solution formulation.

Optionally the formulation may comprise other known pharmaceutical acceptable additives or excipients which are substantially inert materials which are non-toxic and do not interact in negative manner with other components of the formulation. In particular, the formulation may comprise one or more solvents, surfactants, carbohydrate, phospholipid, polymer, wetting agent, stabilizers, lubricants, or low volatility components.

Among the stabilizers, it is envisaged to use a suitable amount of an acid which may be organic or inorganic acid (mineral acids) which may be selected from pharmaceutically acceptable monoprotic or polyprotic acid, such as (but not limited to): hydrogen halides (hydrochloric acid, hydrobromic acid, hydroiodic acid, etc.), phosphoric acid, nitric acid, sulphuric acid, and halogen oxoacids.

Low volatility components are useful in order to increase the mass median aerodynamic diameter (MMAD) of the aerosol particles upon actuation of the inhaler and/or to improve the solubility of the active ingredient in the propellant/solvent system.

The low volatility component, when present, has a vapour pressure at 25° C. lower than 0.1 kPa, preferably lower than 0.05 kPa. Examples of low-volatility components are esters such as isopropyl myristate, ascorbyl myristate, tocopherol esters; glycols such as propylene glycol, polyethylene glycol; or polyols such as glycerol; and surface active agents such as saturated organic carboxylic acids (e.g. lauric, myristic, stearic acid) and unsaturated carboxylic acids (e.g. oleic or ascorbic acid). The amount of low volatility component may vary from 0.1 to 10% w/w, preferably from 0.5 to 5% (w/w), more preferably from 1 and 2% (w/w), based on the entire weight of the formulation. In another embodiment, an amount of water comprised between 0.005 and 0.3% (w/w), based on the total weight of the formulation, may optionally be added to the formulations in order to favourably affect the solubility of the active ingredient without increasing the MMAD of the aerosol droplets upon actuation.

Other features of the invention will become apparent in the course of the following descriptions of exemplary embodiments which are given for illustration of the invention and are not intended to be limiting thereof.

EXAMPLES

Example 1

A range of actuators according to the present invention, terminating in a mouthpiece opening through which the user inhales, comprising a central circular opening of a defined width and distance from the nozzle channel external aperture were designed and manufactured. In particular said opening was designed on a tubular element to be securely snapped into place with the external mouthpiece portion of a conventional actuator 1 of FIG. 1a or 1b as shown in FIGS. 2a and 2b, wherein the basic premise of the design and the respective diameter d and distance D of the tested geometries are represented.

The tubular elements were manufactured in polypropylene (PP), the same material of the actuator. All the tubular elements were fitted on actuators with 0.30 mm nozzle channel diameter. The actuators provided with the tubular element based on FIGS. 2a and 2b were tested with respect to a conventional actuator of FIGS. 1a and 1b with 0.30 mm nozzle channel diameter.

The experiments used pressurised solution formulations of beclometasone dipropionate (BDP) 25 μg/actuation in HFA 134a ethanol, added with different amount of glycerol, as low volatility component, to simulate formulations emitting, after evaporation, fine, medium and coarse aerosol particles.

Each formulation, detailed in Table 1, was manufactured according to WO 98/56349A1, which is incorporated herein by reference in its entirety, packaged in a standard aluminium 19 ml canister, fitted with a conventional 63 μl valve.

TABLE 1

Formulation compositions using HFA 134a (13.6 g fill weight).

| Formulation | BDP Dose (μg/act.) | Ethanol content (% w/w) | Glycerol content (% w/w) | HFA 134a content (% w/w) |
|---|---|---|---|---|
| Fine formulation | 25 | 5 | 0 | 95 |
| Medium formulation | 25 | 10 | 0.2 | 89.8 |
| Coarse formulation | 25 | 15 | 0.7 | 84.3 |

The tested actuators had the dimensions of the central rounded opening detailed in Table 2

TABLE 2

Actuator dimensions.

| Actuator tested | Diameter d (mm) | Distance from nozzle channel aperture D (mm) | Ratio diameter/ distance (d/D) |
|---|---|---|---|
| Actuator 1 | 5 | 16 | 0.31 |
| Actuator 2 | 8 | 28.5 | 0.28 |
| Actuator 3 | 10 | 38.5 | 0.26 |
| Actuator 4 | 11 | 41 | 0.27 |

Drug delivery characterization of the actuators according to the invention, in comparison with a conventional actuator, in conjunction with the BDP formulation of Table 1, was determined with a Fast Screening Andersen (FSA) cascade impactor (from Copley Scientific) an abbreviated version of the standard full-resolution Andersen Cascade Impactor (ACI) a suitably modified version of the Andersen Cascade Impactor (Apparatus D, European Pharmacopoeia 8$^{th}$ Ed. Suppl 8.5, 2014, which is incorporated herein by reference in its entirety).

Two replications for each configuration were performed. The procedure according to common Pharmacopoeias, was conducted at a flow rate of 28.3 (±5%) L/min and the drug deposition in each stage and in the induction port was quantified by HPLC/UV (High-Performance Liquid Chromatography/UV detection).

The performance of each actuator with the three different kinds of formulations (Fine, Medium, Coarse) in terms of Induction Port (IP) deposition, Fine Particle Dose (FPD) and extra-Fine Particle Dose (e-FPD) is reported in the following Tables 3a, 3b, 3c and 3d.

TABLE 3a

Performance data for Actuator 1 according to the invention in comparison with a Conventional Actuator.

|  | IP (μg/act) | FPD (μg/act) | e-FPD (μg/act) |
|---|---|---|---|
| Fine Formulation |  |  |  |
| Conventional Actuator | 6.2 | 14.6 | 11.7 |
| Actuator 1 | 5.2 | 9.2 | 8.5 |
| % Act 1 vs Conv Act | −16 | −37 | −27 |
| Coarse Formulation |  |  |  |
| Conventional Actuator | 13.7 | 5.4 | 1.4 |
| Actuator 1 | 9.4 | 3.4 | 1.3 |
| % Act 1 vs Conv Act | −31 | −37 | −7 |

TABLE 3b

Performance data for Actuator 2 according to the invention in comparison with a Conventional Actuator.

|  | IP (µg/act) | FPD (µg/act) | e-FPD (µg/act) |
|---|---|---|---|
| Fine Formulation |  |  |  |
| Conventional Actuator | 6.2 | 14.6 | 11.7 |
| Actuator 2 | 3.7 | 11.5 | 9.7 |
| % Act 2 vs Conv Act | −40 | −21 | −17 |
| Medium |  |  |  |
| Conventional Actuator | 9.7 | 8.6 | 3.0 |
| Actuator 2 | 9.1 | 5.0 | 1.4 |
| % Act 2 vs Conv Act | −6 | −42 | −53 |
| Coarse Formulation |  |  |  |
| Conventional Actuator | 13.7 | 5.4 | 1.4 |
| Actuator 2 | 5.7 | 8.6 | 3.4 |
| % Act 2 vs Conv Act | −58 | +59 | +143 |

TABLE 3c

Performance data for Actuator 3 according to the invention in comparison with a Conventional Actuator.

|  | IP (µg/act) | FPD (µg/act) | e-FPD (µg/act) |
|---|---|---|---|
| Fine Formulation |  |  |  |
| Conventional Actuator | 6.2 | 14.6 | 11.7 |
| Actuator 3 | 2.5 | 11.7 | 9.6 |
| % Act 3 vs Conv Act | −60 | −20 | −18 |
| 95% IC Conv Act | 1.7 | 1.5 | 0.9 |
| 95% IC Act 3 | 1.4 | 1.2 | 0.7 |
| Medium Formulation |  |  |  |
| Conventional Actuator | 9.7 | 8.6 | 3.0 |
| Actuator 3 (µg/act) | 6.1 | 7.3 | 3.0 |
| % Act 3 vs Conv Act | −37 | −15 | 0 |
| 95% IC Conv Act | 1.7 | 1.5 | 0.9 |
| 95% IC Act 3 | 1.1 | 1.0 | 0.6 |
| Coarse Formulation |  |  |  |
| Conventional Act | 13.7 | 5.4 | 1.4 |
| Act 3 | 6.2 | 5.2 | 1.6 |
| % Act 3 vs Conv Act | −55 | −4 | +14 |
| 95% IC Conv Act | 1.7 | 1.5 | 0.9 |
| 95% IC Act 3 | 1.3 | 1.1 | 0.7 |

TABLE 3d

Performance data for Actuator 4 according to the invention in comparison with a Conventional Actuator.

|  | IP (µg/act) | FPD (µg/act) | e-FPD (µg/act) |
|---|---|---|---|
| Fine Formulation |  |  |  |
| Conventional Actuator | 6.2 | 14.6 | 11.7 |
| Actuator 4 | 2.0 | 12.5 | 10.3 |
| % Act 4 vs Conv Act | −68 | −14 | −12 |
| Coarse Formulation |  |  |  |
| Conventional Actuator | 13.7 | 5.4 | 1.4 |
| Acuator 4 | 6.1 | 4.7 | 1.3 |
| % Act 4 vs Conv Act | −37 | −45 | −57 |

The results showed that through changes in the mouthpiece actuator shape the oropharyngeal deposition of the aerosol (corresponding to the Induction Port (IP) deposition) could be significantly decreased, with respect to a conventional actuator, without affecting the aerodynamic particle size distribution performance.

In particular the configuration of Actuator 3 with a circular mouthpiece opening having a diameter 10 mm placed at a distance of 38.5 mm from the nozzle channel aperture allows to halve the IP deposition keeping almost constant the fine and extra-fine particle dose of pressurized solution formulations independently from the fact they may originate fine, medium or coarse particles depending from their level in low volatility component.

Example 2

Drug delivery tests on the actuator according to the present invention were performed by using three different pMDI products available in the market and compared with the data obtained with their respective actuator with which they are sold.

The tested actuator was the conventional actuator of the marketed product provided with the tubular element according to the invention with a central circular opening of 10 mm diameter (d), at a distance (D) of 38.5 mm from the nozzle channel aperture of the nozzle block, corresponding to a ratio diameter/distance d/D=0.26.

The tested products were:
(1) Atimos pMDI, containing a formulation of formoterol fumarate (FF), 12 µg/actuation, dissolved in a solution of FIFA 134a, ethanol and hydrochloric acid;
(2) Foster pMDI, containing a formulation of the combination of formoterol fumarate (FF), 6 µg/actuation, and beclomethasone dipropionate (BDP) 100 µg/actuation both dissolved in a solution of HFA 134a, ethanol and hydrochloric acid; and
(3) Clenil 100 pMDI, containing a formulation of beclometasone dipropioate (BDP), 100 µg/actuation, dissolved in a solution of HFA 134a, ethanol and glycerol as low volatility component.

All the actuators had 0.30 mm nozzle channel diameter.

The drug delivery characterization of the actuators according to present the invention, in comparison with the conventional actuator was conducted in vitro using a Next Generation Impactor (NGI) fitted with an induction port (Apparatus E, European Pharmacopoeia 8th Ed. Suppl 8.5, 2014, which is incorporated herein by reference in its entirety) set at a flow rate of 30 L/min.

Three replicaations for each product were performed except for Foster wherein four replications were used.

Validated HPLC methods were used for the determination of the two drugs.

The performance of each actuator with the three different products in terms of Induction Port (IP) deposition, Fine Particle Dose (FPD) and extra-Fine Particle Dose (e-FPD) plus the respective standard deviations (±SD) and percent variation between actuator according to the invention versus conventional actuator is reported in the following Tables 4a to 4c.

TABLE 4a

Performance data of Atimos pMDI (FF 12 µg/actuation) delivered by the actuator of the present invention provided with the tubular element with a central rounded opening of d = 10 mm and D = 38.5 mm (d/D = 0.26) in comparison with its conventional actuator.

| ATIMOS (12 µg/act) | IP ± SD | FPD ± SD | e-FPD ± SD |
|---|---|---|---|
| Conventional Actuator (µg/act) | 5.02 ± 0.67 | 3.43 ± 0.68 | 3.16 ± 0.69 |
| Actuator with tubular element of the presentinvention (µg/act) | 1.85 ± 0.96 | 3.30 ± 0.69 | 3.03 ± 0.74 |

TABLE 4a-continued

Performance data of Atimos pMDI (FF 12 μg/actuation)
delivered by the actuator of the present invention
provided with the tubular element with a central rounded
opening of d = 10 mm and D = 38.5 mm (d/D = 0.26)
in comparison with its conventional actuator.

| ATIMOS (12 μg/act) | IP ± SD | FPD ± SD | e-FPD ± SD |
|---|---|---|---|
| % Act. of invention vs Conventional Act. | −63 | −4 | −4 |

TABLE 4b

Performance data of Foster pMDI (FF 6 μg/actuation and BDP
100 μg/actuation) delivered by the actuator of the present invention
provided with the tubular element with a central rounded
opening of d = 10 mm and D = 38.5 mm (d/D = 0.26)
n comparison with its conventional actuator.

| FOSTER (6-100 μg/act) | IP ± SD | FPD ± SD | e-FPD ± SD |
|---|---|---|---|
| Conventional Actuator | | | |
| Formoterol (μg/act) | 2.64 ± 0.06 | 1.78 ± 0.22 | 1.29 ± 0.23 |
| BDP (μg/act) | 46.96 ± 1.77 | 29.10 ± 0.28 | 19.27 ± 0.46 |
| Actuator with tubular element of the present invention | | | |
| Formoterol (μg/act) | 1.41 ± 0.09 | 1.43 ± 0.12 | 0.98 ± 0.08 |
| BDP (μg/act) | 24.95 ± 1.24 | 26.00 ± 1.39 | 17.25 ± 1.33 |
| % Act. of invention vs Conventional Act. | | | |
| Formoterol | −46 | −19 | −24 |
| BDP | −47 | −11 | −10 |

TABLE 4c

Performance data of Clenil pMDI (BDP 100 μg/actuation)
delivered by the actuator of the present invention
provided with the tubular element with a central rounded
opening of d = 10 mm and D = 38.5 mm (d/D = 0.26) in
comparison with its conventional actuator.

| CLENIL (100 μg/act) | IP ± SD | FPD ± SD | e-FPD ± SD |
|---|---|---|---|
| Conventional Actuator (μg/act) | 48.88 ± 3.63 | 25.63 ± 0.38 | 7.11 ± 0.20 |
| Act. with tubular element of the present invention (μg/act) | 28.30 ± 2.92 | 24.37 ± 0.40 | 7.08 ± 0.59 |
| % Act. of invention vs Conventional Act. | −42 | −5 | 0 |

The results confirmed that the actuator according to the present invention significantly reduced by about −63%, −46%/−47%, and −42% the induction port (IP) deposition (corresponding to the amount of "non-respirable", larger aerosol particles that, upon inhalation, impact within the mouth and throat of the patient) respectively of Atimos, Foster, and Clenil active ingredients in comparison with a conventional actuator.

On the contrary, no significant differences were shown in the fine particle dose (FPD) between the actuator of the invention and conventional actuators. In fact, according to the EMA (European Medicines Agency) guideline CPMP/EWP/4151/00 Rev. 1, which is incorporated herein by reference in its entirety, differences within ±15% are considered equivalent. The only exception was for formoterol in Foster which resulted in −19% which is, however, very close to the limit.

Example 3

Drug delivery investigations on the actuator according to the present invention, consisting of a conventional actuator provided with a tubular element with a central circular opening of 10 mm diameter (d), at a distance (D) of 38.5 mm (d/D=0.26) from the nozzle channel aperture of the nozzle block were also performed by using a pMDI containing a triple combination of three different active ingredients dissolved in the formulation.

In the experiment a solution formulation of beclometasone dipropionate (BDP) 100 μg/actuation, formoterol fumarate (FF), 6 μg/actuation, and glycopyrronium bromide (GLY), 12.5 μg/actuation, detailed in Table 5 and manufactured according to WO 2011076843A1, which is incorporated herein by reference in its entirety, was used. The formulation was packaged in 19 ml canister fitted with a conventional 63 μL valve and a conventional actuator with 0.30 mm orifice diameter.

TABLE 5

Formulation of the combination of Example 3.
(Content % (w/w) means the percent content by
weight of each component with respect to the
total weight of the formulation).

| Component | Mass (μg) per actuation (63 μL) | Content % (w/w) |
|---|---|---|
| BDP | 100 | 0.135 |
| FF | 6 | 0.0081 |
| GLY | 12.5 | 0.0169 |
| Ethanol | 8856 | 12.0000 |
| 1M HCl | 14 | 0.019 |
| HFA 134a | 64811.5 | 87.820 |

All the actuators had 0.30 mm nozzle channel diameter.

The drug delivery characterization of the actuator according to the present invention, in comparison with the conventional actuator was conducted in vitro, as reported for Example 2.

Three replications were performed.

Validated HPLC methods were used for the determination of the three drugs.

The performance of each actuator, in terms of Induction Port (IP) deposition, Fine Particle Dose (FPD) and extra-Fine Particle Dose (e-FPD) plus the respective standard deviations (±SD) and percent variation between actuator according to the invention versus conventional actuator, is reported in the following Table 6.

TABLE 6

Performance data of a triple combination
FF 6, μg/actuation, BDP, 100 μg/actuation, and GLY,
12.5 μg/actuation, delivered by the actuator of the invention
provided with the tubular element with a central
rounded opening of d = 10 mm and D = 38.5 mm
(d/D = 0.26) in comparison with those of a
conventional actuator.

| Triple combin (6-100-12.5 μg/act) | IP ± SD | FPD ± SD | e-FPD ± SD |
|---|---|---|---|
| Conventional Act. | | | |
| FF (μg/act) | 2.93 ± 0.04 | 1.50 ± 0.00 | 0.98 ± 0.02 |
| BDP (μg/act) | 50.00 ± 0.50 | 26.37 ± 0.50 | 17.25 ± 0.39 |
| GLY (μg/act) | 12.72 ± 0.47 | 6.67 ± 0.12 | 4.29 ± 0.04 |

TABLE 6-continued

Performance data of a triple combination
FF 6, μg/actuation, BDP, 100 μg/actuation, and GLY,
12.5 μg/actuation, delivered by the actuator of the invention
provided with the tubular element with a central
rounded opening of d = 10 mm and D = 38.5 mm
(d/D = 0.26) in comparison with those of a
conventional actuator.

| Triple combin (6-100-12.5 μg/act) | IP ± SD | FPD ± SD | e-FPD ± SD |
|---|---|---|---|
| Act. with tubular element of the invention | | | |
| FF (μg/act) | 1.30 ± 0.11 | 1.47 ± 0.21 | 1.02 ± 0.14 |
| BDP (μg/act) | 22.53 ± 1.98 | 25.97 ± 3.19 | 17.69 ± 2.72 |
| GLY (μg/act) | 5.85 ± 0.51 | 6.43 ± 0.78 | 4.33 ± 0.71 |
| % Act. of invention vs Conventional Act. | | | |
| FF | −56 | −2 | +4 |
| BDP | −55 | −2 | +3 |
| GLY | −54 | −4 | +1 |

For all the three active ingredients, there is no significant difference in the fne FPD and e-FPD between the actuator of the invention and a conventional actuator.

For all the three active ingredients, the actuator according to the invention reduced the IP deposition of about 50%.

Example 4

Further drug delivery tests were performed by using the marketed Foster pMDI product of Example 2, containing a formulation of the combination of formoterol fumarate, 6 μg/actuation (FF), and beclometasone dipropionate (BDP), 100 μg/actuation, both dissolved in a solution of HFA 134a, ethanol and hydrochloric acid.

The product was tested with the conventional actuator of the marketed product provided with two different tubular elements of FIGS. 4a-4f according to the invention, with a central circular opening of 10 mm and 11 mm diameter (d), at a distance (D) respectively of 38.5 mm and 42.15 mm from the nozzle channel aperture of the nozzle block (d/D=0.26 in both cases) and produced by 3D-printing with a conventional 3D-printing photopolymer material (RGD875 VeroBlackPlus). The data were compared with those obtained with the conventional actuator with which the product is sold.

The actuators had all a 0.30 mm nozzle channel diameter.

The methods were the same as those described in Example 2, with three replicas performed.

Validated HPLC methods were used for the determination of the two drugs.

The results are reported in the Table 7.

TABLE 7

Performance data of Foster pMDI (formoterol fumarate,
6 μg/actuation, and beclometasone dipropionate, 100 μg/actuation)
delivered by the actuator of the invention provided
with the 3D-printed tubular element with a central
circular openings of d =10 mm; D = 38.5 mm and d = 11 mm;
D = 42.15 in comparison with the conventional actuator.

| FOSTER (6-100 μg/act) | IP ± SD | FPD ± SD | e-FPD ± SD |
|---|---|---|---|
| Conventional Act. | | | |
| FF (μg/act) | 2.34 ± 0.18 | 2.06 ± 0.12 | 1.19 ± 0.12 |
| BDP (μg/act) | 41.99 ± 3.24 | 38.85 ± 2.68 | 22.72 ± 2.33 |
| Act. with 3D-printed tubular element d = 10 mm; D = 38.5 mm | | | |
| FF (μg/act) | 1.01 ± 0.05 | 2.10 ± 0.08 | 1.26 ± 0.01 |
| BDP (μg/act) | 18.81 ± 1.16 | 39.94 ± 0.86 | 23.68 ± 0.33 |
| % difference vs Conventional Act. | | | |
| FF | −57 | +2 | +6 |
| BDP | −55 | +3 | +4 |
| Act. with 3D-printed tubular element d = 11 mm; D = 42.15 mm | | | |
| FF (μg/act) | 0.76 ± 0.13 | 2.06 ± 0.06 | 1.19 ± 0.07 |
| BDP (μg/act) | 16.5 ± 3.85 | 36.5 ± 0.41 | 21.18 ± 0.72 |
| % difference vs Conventional Act. | | | |
| FF | −68 | +0 | 0 |
| BDP | −61 | −6 | −7 |

The data showed that 3D-printed tubular element according to the invention still reduced the induction port deposition of both the active ingredients of values higher than 50% (−55/−57% and −68/−61%) with respect to a conventional actuator but without significatively affecting the particle size distribution performance and in particular the fine and extra-fine particle dose.

Example 5

Drug delivery tests were performed by using the marketed Foster pMDI product of Example 2, containing a formulation of the combination of formoterol fumarate, 6 μg/actuation, (FF) and beclometasone dipropionate (BDP), 100 μg/actuation, both dissolved in a solution of HFA 134a, ethanol and hydrochloric acid.

The product was tested with the conventional actuator of the marketed product provided with the tubular element of FIGS. 5a-5g according to the invention, with a central circular opening of 11 mm diameter (d), at a distance (D) of 45 mm from the nozzle channel aperture of the nozzle block (d/D=0.245) having a cylindrical recess, formed by the central opening edges, facing towards the inside of the mouthpiece portion, at an angle A of 90°, with respect to the plane of the wall defining the central opening, for a length t of 5 mm, produced by 3D-printing with a conventional 3D-printing photopolymer material (RGD875 VeroBlackPlus). The data were compared with those obtained with the conventional actuator with which the product is sold.

The actuators had all a 0.30 mm nozzle channel diameter.

The methods used for the study were the same as those described in Example 2 with three replications.

Validated HPLC methods were used for the determination of the two drugs.

The results are reported in the Table 8.

TABLE 8

Performance data of Foster pMDI (formoterol fumarate 6 µg/actuation and beclometasone dipropionate 100 µg/actuation) delivered by the actuator of the present invention provided with the 3D-printed tubular element with a central circular opening of diameter d = 11 mm; at a distance D = 45 mm; with a cylindrical recess at an angle A = 90° with respect to the plane of the wall defining the central opening, for a length t = 5 mm in comparison with the conventional actuator.

| FOSTER (6-100 µg/act) | IP ± SD | FPD ± SD | e-FPD ± SD |
|---|---|---|---|
| Conventional Act. | | | |
| FF (µg/act) | 2.02 ± 0.32 | 2.10 ± 0.12 | 1.20 ± 0.05 |
| BDP (µg/act) | 39.83 ± 3.26 | 39.83 ± 3.26 | 23.91 ± 1.42 |
| Act. with 3D-printed tubular element d = 10 mm; D = 38.5 mm; A = 90; t = 5 mm | | | |
| FF (µg/act) | 0.56 ± 0.11 | 2.28 ± 0.08 | 1.29 ± 0.08 |
| BDP (µg/act) | 9.04 ± 1.04 | 42.24 ± 0.86 | 25.18 ± 0.61 |
| % difference vs Conventional Act. | | | |
| FF | −72 | +8 | +6 |
| BDP | −74 | +6 | +7 |

The data showed that an optimised 3D-printed tubular element according to the invention having a cylindrical recess, facing towards the inside of the mouthpiece portion, still reduced the induction port deposition of both the active ingredients to values higher than 70% (−72% and −74%) with respect to a conventional actuator but without significatively affecting the particle size distribution performance and in particular the fine and extra-fine particle dose (differences lower than 10%).

Example 6

Drug delivery tests were performed by using the formulation of Example 3 (Table 5, constituted by a pressurised solution formulation of beclometasone dipropionate (BDP), 100 µg/actuation, formoterol fumarate (FF), 6 µg/actuation, and glycopyrronium bromide (GLY) 12.5 µg/actuation.

The product, packaged in 19 ml canister fitted with a conventional 63 µL valve was tested with a conventional actuator with 0.30 mm orifice provided with the tubular element of FIGS. 5a-5g according to the invention, having a central circular opening of 11 mm diameter (d), at a distance (D) of 45 mm from the nozzle channel aperture of the nozzle block (d/D=0.245) having a cylindrical recess at an angle A of 90°, with respect to the plane of the wall defining the central opening, for a length (t) of 5 mm, produced by 3D-printing with a conventional 3D-printing photopolymer material (RGD875 VeroBlackPlus). The data were compared with those obtained with the conventional actuator only.

The methods were the same as those described in Example 3 with three replications.

Validated HPLC methods were used for the determination of the three drugs.

The results are reported in the Table 9.

TABLE 9

Performance data of a triple combination FF 6, µg/actuation, BDP, 100 g/actuation, and GLY, 12.5 µg/actuation, delivered by the delivered by the actuator of the present invention provided with the 3D-printed tubular element with a central circular opening of diameter d = 11 mm; at a distance D = 45mm; with a cylindrical recess at an angle A of 90° with respect to the plane of the wall defining the central opening, for a length t = 5 mm in comparison with the conventional actuator.

| Triple combin (6-100-12.5 µg/act) | IP ± SD | FPD ± SD | e-FPD ± SD |
|---|---|---|---|
| Conventional Act. | | | |
| FF (µg/act) | 2.49 ± 0.22 | 2.07 ± 0.08 | 1.05 ± 0.11 |
| BDP (µg/act) | 41.37 ± 3.42 | 37.50 ± 1.38 | 19.98 ± 0.68 |
| GLY (µg/act) | 5.14 ± 0.58 | 4.57 ± 0.19 | 2.40 ± 0.09 |
| Act. with tubular element of the invention | | | |
| FF (µg/act) | 0.65 ± 0.05 | 1.87 ± 0.21 | 0.93 ± 0.12 |
| BDP (µg/act) | 10.63 ± 0.99 | 35.42 ± 2.86 | 18.98 ± 2.87 |
| GLY (µg/act) | 1.32 ± 0.14 | 4.25 ± 0.42 | 2.26 ± 0.40 |
| % difference vs Conventional Act. | | | |
| FF | −74 | −10 | −11 |
| BDP | −74 | −6 | −5 |
| GLY | −74 | −7 | −6 |

The data showed that an optimised 3D-printed tubular element according to the present invention having a cylindrical recess, facing towards the inside of the mouthpiece portion, still reduced the induction port deposition of a triple combination of active ingredients in solution to values higher than 70% (and in particular 74% for all the three components) with respect to a conventional actuator, but without significantly affecting the particle size distribution performance and in particular the fine and extra-fine particle dose (with differences lower or around 10%).

Example 7: In-Use Study Simulation

The aim of the study was to estimate the risk that, during the patient use of the device, the coarse particles of the medicament doses sprayed, but retained in the actuator, after cumulative administrations, may escape from the actuator in form of high spots reaching the patient mouth or oropharynx. These high spots may contain high amounts of active ingredients and may be swallowed causing potential safety risk to patients.

The test was conducted quantifying the amount of active ingredients particles which could detach from the actuator during a patient use simulation study. The study was carried out on actuators provided with the tubular element according to the invention described in Example 5 (FIGS. 5a-5g, diameter d=11 mm, at a distance D=45 mm from the nozzle channel aperture, having a cylindrical recess at an angle A=90°) by firing two actuations twice daily, up to end of labelled canister life (180 actuations in a 45-days treatment) of the currently marketed Foster pMDI described in Example 2 (containing as active ingredients FF 6, µg/actuation, and BDP, 100 µg/actuation). The tests were performed at 6 different time points corresponding to 6 different canister lives: after 32, 60, 88, 120, 148, and 180 cumulative actuations. Two parameters were determined at each time point: the amount of active ingredients migrated and the amount of active ingredients residues.

The active ingredients particles migrated were evaluated recovering in a Next Generation Impactor (NGI) cup the particles detached from the actuators provided with the tubular element according to the invention, after 300 automatic taps, in 70 seconds, using Autotap tap density analyser (Quantachrome). The recovered particles were then dissolved with suitable solvent and quantified by a validated HPLC/UV method.

The amount of active ingredients residues, still present both in the actuator and in the tubular element (not detached), were recovered rinsing the actuator and the tubular element with solvent and quantifying the active ingredients by validated HPLC/UV method.

Three replications both for reference (conventional, actuator only) and actuator with the tubular element according to the invention were carried out. The mean results are reported in Table 10.

The data showed that despite the higher amount of active ingredients collected, less than 3 µg were able to migrate (detached) from the internal wall of the actuator with the tubular element according to the invention up to the end of canister life. The migrated amount is comparable to the amount migrated from the conventional (reference actuator). The risk of exposure of a patient to high spots, evaluated as amount of drug particles migration during patient use was therefore negligible.

TABLE 10

Result of In-use study simulation. Determining the amount of active ingredients migrated/residues after cumulative actuations of Foster pMDI formulation (formoterol fumarate (FF), 6 µg/actuation, and beclometasone dipropionate (BDP), 100 µg/actuation) through the actuator of the present invention, provided with the tubular element with a central circular opening of diameter d = 11 mm; at a distance D = 45 mm; with a cylindrical recess at an angle A = 90° with respect to the plane of the wall defining the central opening, for a length t = 5 mm in comparison with the conventional (reference) actuator.

| | | After 32 acts | After 60 acts | After 88 acts | After 116 acts | After 144 acts | After 180 acts |
|---|---|---|---|---|---|---|---|
| REFERENCE (Actuator only) | migrated-BDP (µg) | 1 | 1 | 0 | 1 | 3 | 1 |
| | residue-BDP (µg) | 114 | 542 | 1145 | 938 | 1574 | 1885 |
| | migrated-FF (µg) | 0 | 0 | 0 | 0 | 0 | 0 |
| | residue-FF (µg) | 16 | 62 | 116 | 95 | 166 | 157 |
| ACTUATOR plus Tubular Element | migrated-BDP (µg) | 0 | 2 | 0 | 1 | 1 | 1 |
| | residue-BDP (µg) | 827 | 2163 | 2620 | 3390 | 3932 | 5588 |
| | migrated-FF (µg) | 0 | 0 | 0 | 0 | 0 | 0 |
| | residue-FF (µg) | 104 | 168 | 231 | 331 | 432 | 553 |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An actuator for an aerosol inhalation device that is a pressurized metered dose inhaler, comprising:
   a housing adapted to receive an aerosol canister containing a pressurised medicament formulation, provided with a metering valve having a hollow valve stem with a longitudinal axis, the housing comprising a mouthpiece;
   a nozzle block defining a valve stem receptacle, an expansion chamber or sump, a nozzle channel having a central longitudinal axis, and an aperture to propel an aerosol formulation towards the mouthpiece; and
   a tubular element configured to be removable from the mouthpiece, the tubular element comprising:
   (1) a proximal opening of suitable shape and dimensions adapted to be securely snapped into place with the mouthpiece, the proximal opening and a proximal end portion of the tubular element form a proximal most end of the tubular element,
   (2) a mouthpiece portion, the mouthpiece portion comprising a central rounded mouthpiece opening, the central rounded mouthpiece opening being on an opposite side from the proximal opening, the mouthpiece portion having a central longitudinal axis located at an angle in a range from approximately 90° to approximately 120° to a direction of the longitudinal axis of the hollow valve stem, and
   (3) a planar distal end wall and one or more external sidewalls,
   wherein the planar distal end wall and the one or more external sidewalls define an interior space,
   wherein said central rounded mouthpiece opening comprises a diameter d from 5 to 14 mm and at a distance D from 16 to 58 mm from an external aperture of said nozzle channel and a central axis of the central rounded mouthpiece opening is aligned with the central longitudinal axis of said mouthpiece portion and coinciding with the central longitudinal axis of said nozzle channel,
   wherein said interior space connects the proximal opening to the central rounded mouthpiece opening, the interior space comprises a first section closer to the proximal opening than the central rounded mouthpiece opening and a second section closer to the central rounded mouthpiece opening than the proximal opening, and the first section comprises a diameter that is larger than a diameter of the second section,
   wherein an internal extension extends at an angle of any value in the range from 30° to 150° with respect to a plane of the planar distal end wall defining said central rounded mouthpiece opening,
   wherein the internal extension extends from the planar distal end wall toward the nozzle block so as to form a void between a sidewall of said internal extension and one or more lateral external sidewalls, the void being radially outward of the sidewall of said internal extension, wherein said central rounded mouthpiece opening is configured on a planar surface of the planar distal end wall and is formed by an interior curve surface of the planar distal end wall, wherein the planar surface is normal to the one or more lateral external sidewalls of said mouthpiece portion, wherein said internal extension extends from the planar surface, wherein said central rounded mouthpiece opening configured on the planar surface is an opening of the mouthpiece portion at which the medicament formulation exits the mouthpiece portion and the aerosol inhaler actuator, wherein the central rounded mouthpiece opening and the planar surface are aligned such that the central rounded mouthpiece opening and the planar surface form a distal most end of the tubular element, and wherein the internal extension comprises a longitudinal length that is shorter than a longitudinal length of the interior space.

2. The actuator according to claim 1, wherein the central rounded mouthpiece opening has a circular, elliptical, or ovoidal shape.

3. The actuator according to claim 1, wherein the central rounded mouthpiece opening has a circular shape.

4. The actuator according to claim 1, wherein the diameter d is from 8 to 12 mm.

5. The actuator according to claim 4, wherein the central rounded mouthpiece opening is at the distance D from the external aperture of from 38.5 to 54.1 mm.

6. The actuator according to claim 1, wherein the central rounded mouthpiece opening is at the distance D from the external aperture of from 28.5 to 58 mm.

7. The actuator of claim 1, wherein a ratio d/D between the diameter d in mm of the central rounded mouthpiece opening of the mouthpiece portion and the distance D in mm from the external aperture is from 0.09 to 0.88.

8. The actuator of claim 1, wherein said sidewall of the internal extension forms the void at the angle of 90°±2° with respect to the plane of the planar distal end wall defining said central rounded mouthpiece opening.

9. An inhaler, comprising an aerosol canister, containing a pressurized medicament formulation, having a metering valve and a valve stem capable of being fitted into said valve stem receptacle of an actuator according to claim 1.

10. A method for the reduction of the non-respirable dose and consequent potential oro-pharyngeal deposition of a dispensed aerosol formulation on actuation of a metered-dose inhaler, said method comprising providing said metered-dose inhaler with an actuator according to claim 1.

11. A method of treating a disease of the respiratory tract, comprising administering to a subject in need thereof an effective amount of a medicament from an inhaler comprising an actuator according to claim 1.

12. The actuator of claim 1, wherein the void is configured as a receptacle to receive non-respirable particles or droplets of the aerosol formulation output from the aperture.

13. The actuator of claim 1, wherein an area of the central rounded mouthpiece opening is 64 to 113 mm$^2$.

14. The actuator according to claim 1, wherein the angle of the central longitudinal axis is greater than 90° and less than 120° to the direction of the longitudinal axis of the hollow valve stem.

15. A tubular element, comprising:
(1) a proximal opening of suitable shape and dimensions adapted to be securely snapped into place with a mouthpiece of an aerosol inhaler actuator that is a pressurized metered dose inhaler, the proximal opening and a proximal end portion of the tubular element forming a proximal most end of the tubular element, the inhaler comprising:
  (a) a housing adapted to receive an aerosol canister containing a pressurized medicament formulation, provided with a metering valve having a hollow valve stem with a longitudinal axis, and
  (b) a nozzle block defining a valve stem receptacle, an expansion chamber or sump, a nozzle channel having a central longitudinal axis, and an aperture to propel an aerosol formulation towards an opening of the mouthpiece;
(2) a mouthpiece portion comprising central rounded mouthpiece opening, the central rounded mouthpiece opening being on an opposite side from the proximal opening, the mouthpiece portion having a central longitudinal axis located at an angle in a range from approximately 90° to approximately 120° to a direction of the longitudinal axis of the hollow valve stem; and
(3) a planar distal end wall and one or more external sidewalls, wherein the planar distal end wall and the one or more external sidewalls define an interior space, wherein said central rounded mouthpiece opening comprises a diameter d from 5 to 14 mm and at a distance D from 16 to 58 mm from an external aperture of said nozzle channel and a central axis of the central rounded mouthpiece opening is aligned with the central longitudinal axis of said mouthpiece portion and coinciding with the central longitudinal axis of said nozzle channel, wherein said interior space connects the proximal opening to the central rounded mouthpiece opening, the interior space comprises a first section closer to the proximal opening than the central rounded mouthpiece opening and a second section closer to the central rounded mouthpiece opening than the proximal opening, and the first section comprises a diameter that is larger than a diameter of the second section, wherein an internal extension extends at an angle of any value in the range from 30° to 150° with respect to a plane of the planar distal end wall defining said central rounded mouthpiece opening, wherein the internal extension extends from the planar distal end wall toward the nozzle block so as to form a void between a sidewall of said internal extension and one or more lateral external sidewalls, the void being radially outward of the sidewall of said internal extension, wherein said central rounded mouthpiece opening is configured on a planar surface of the planar distal end wall and is formed by an interior curve surface of the planar distal end wall, wherein the planar surface is normal to the one or more lateral external sidewalls of said mouthpiece portion, wherein said internal extension extends from the planar surface, wherein said central rounded mouthpiece opening configured on the planar surface is an opening of the mouthpiece portion at which the medicament formulation exits the mouthpiece portion and the aerosol inhaler actuator, wherein the central rounded mouthpiece opening and the planar surface are aligned such that the central rounded mouthpiece opening and the planar surface form a distal most end of the tubular element, and wherein the internal extension comprises a longitudinal length that is shorter than a longitudinal length of the interior space.

16. The tubular element according to claim 15, wherein said tubular element is molded of a same material as said actuator or is molded of a material that is different from a material of the actuator.

17. An inhaler, comprising an aerosol canister, containing a pressurized medicament formulation, having a metering valve and a valve stem capable of being fitted into said valve stem receptacle of an actuator provided with a tubular element of claim 15.

18. A tubular element, comprising:

(1) a proximal opening of suitable shape and dimensions adapted to be securely snapped into place with a mouthpiece of an aerosol inhaler actuator that is a pressurized metered dose inhaler, the proximal opening and a proximal end portion of the tubular element forming a proximal most end of the tubular element, the inhaler comprising:

(a) a housing adapted to receive an aerosol canister containing a pressurized medicament formulation, provided with a metering valve having a hollow valve stem with a longitudinal axis, and (b) a nozzle block defining a valve stem receptacle, an expansion chamber or sump, a nozzle channel having a central longitudinal axis, and an aperture to propel an aerosol formulation towards an opening of the mouthpiece;

(2) a mouthpiece portion comprising central circular mouthpiece opening, the central circular mouthpiece opening being on an opposite side from the proximal opening, the mouthpiece portion having a central longitudinal axis located at an angle in a range from approximately 90° to approximately 120° to a direction of the longitudinal axis of the hollow valve stem; and (3) a planar distal end wall and one or more lateral external sidewalls, wherein the planar distal end wall and the one or more external sidewalls define an interior space, wherein said central circular mouthpiece opening is (i) of an internal diameter d which is about 9, 10, 11, or 12 mm, and (ii) at a distance D of about 38.5, 41.0, 45.0, 50.3, or 54.1 mm from an external aperture of said nozzle channel and a central axis of the central circular mouthpiece opening is aligned with the central longitudinal axis of said mouthpiece portion and coinciding with the central longitudinal axis of the nozzle channel, wherein said interior space connects the proximal opening to the central circular mouthpiece opening, the interior space comprises a first section closer to the proximal opening than the central circular mouthpiece opening and a second section closer to the central circular mouthpiece opening than the proximal opening, and the first section comprises a diameter that is larger than a diameter of the second section, wherein an internal sidewall extends from the planar distal end wall into the interior space forming a cylindrical recess at an angle of 90° with respect to a plane of the planar distal end wall defining the said central circular mouthpiece opening, the recess comprising a length t of 4, 5, or 6 mm, wherein said mouthpiece defines a void between the internal sidewall and the one or more lateral external sidewalls, the void being radially outward of the internal sidewall, wherein said central circular mouthpiece opening is configured on a planar surface of the planar distal end wall and is formed by an interior curve surface of the planar distal end wall, wherein the planar surface is normal to the one or more lateral external sidewalls of said mouthpiece portion, wherein said central circular mouthpiece opening configured on the planar surface is an opening of the mouthpiece portion at which the medicament formulation exits the mouthpiece portion and the aerosol inhaler actuator, wherein the central circular mouthpiece opening and the planar surface are aligned such that the central circular mouthpiece opening and the planar surface form a distal most end of the tubular element, and wherein the internal sidewall comprises a longitudinal length that is shorter than a longitudinal length of the interior space.

19. An inhaler, comprising an aerosol canister, containing a pressurized medicament formulation, having a metering valve and a valve stem capable of being fitted into said valve stem receptacle of an actuator provided with a tubular element of claim 18.

* * * * *